US012653816B2

(12) United States Patent
Cheong et al.

(10) Patent No.: US 12,653,816 B2
(45) **Date of Patent: *Jun. 16, 2026**

(54) COMPOSITION FOR INHIBITING GROWTH OF CANCER STEM CELLS

(71) Applicant: INDUSTRY-ACADEMIC COOPERATION FOUNDATION, YONSEI UNIVERSITY, Seoul (KR)

(72) Inventors: Jae-Ho Cheong, Seoul (KR); Jae-Woo Kim, Seoul (KR); Bo Kyung Yoon, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 361 days.

This patent is subject to a terminal disclaimer.

(21) Appl. No.: 18/259,944

(22) PCT Filed: Dec. 29, 2021

(86) PCT No.: PCT/KR2021/020116

§ 371 (c)(1), (2) Date: Jun. 29, 2023

(87) PCT Pub. No.: WO2022/146010

PCT Pub. Date: Jul. 7, 2022

(65) Prior Publication Data

US 2024/0100037 A1 Mar. 28, 2024

(30) Foreign Application Priority Data

Dec. 29, 2020 (KR) ........................ 10-2020-0186256

(51) Int. Cl.

| | |
|---|---|
| ***A61K 31/4545*** | (2006.01) |
| ***A61K 31/4525*** | (2006.01) |
| ***A61K 45/06*** | (2006.01) |
| ***A61P 35/00*** | (2006.01) |
| ***G01N 33/50*** | (2006.01) |

(52) U.S. Cl.

CPC ...... *A61K 31/4545* (2013.01); *A61K 31/4525* (2013.01); *A61K 45/06* (2013.01); *A61P 35/00* (2018.01); *G01N 33/5011* (2013.01); *G01N 33/5073* (2013.01)

(58) Field of Classification Search

None

See application file for complete search history.

(56) References Cited

U.S. PATENT DOCUMENTS

2016/0145251 A1 5/2016 Larsen

OTHER PUBLICATIONS

He et al., "The Wnt-β-catenin signaling regulated MRTF-A transcription to activate migration-related genes in human breast cancer cells," Oncotarget, 9(20), 15239-15251 (2018).

Meng et al., "MRTF-A mediates the activation of COL1A1 expression stimulated by multiple signaling pathways in human breast cancer cells," Biomedicine & Pharmacotherapy, 104, 718-728 (2018).

Zhunag et al., "miR-219a-5p inhibits breast cancer cell migration and epithelial-mesenchymal transition by targeting myocardin-related transcription factor A," Acta Biochimica et Biophysica Sinica, 49(12), 1112-1121 (2017).

International Search Report (translation) and Written Opinion (machine translation) in International Patent Application No. PCT/KR2021/020116, dated Apr. 11, 2022.

*Primary Examiner* — Alicia L Otton

(74) *Attorney, Agent, or Firm* — McDonnell Boehnen Hulbert & Berghoff LLP

(57) ABSTRACT

A composition according to the present invention is capable of inhibiting the growth of cancer cells and cancer stem cells, and also is capable of very effectively inhibiting the metastasis of cancer cells to other tissues. Thus, the composition may be very effectively used not only for the prevention, amelioration or treatment of cancer, but also for the inhibition of cancer metastasis.

5 Claims, 4 Drawing Sheets

COMPOSITION FOR INHIBITING GROWTH OF CANCER STEM CELLS

CROSS-REFERENCE TO RELATED APPLICATIONS

This application is a U.S. National Stage entry of International Patent Application no. PCT/KR2021/020116, filed Dec. 29, 2021, which claims the benefit of priority of Korean Patent Application no. 10-2020-0186256, filed Dec. 29, 2020.

TECHNICAL FIELD

The present invention relates to a composition for treating cancer that inhibits growth of cancer stem cells and metastasis of cancer cells.

BACKGROUND ART

Cancer is a very fatal disease that can threaten the life of an individual by causing cells constituting a tissue to proliferate abnormally and indefinitely to form a tumor so that the organ is unable to perform its normal functions. In 2017, the number one cause of death in Koreans was malignant neoplasm (cancer), and 27.6% of all deaths were due to cancer. In particular, gastric cancer (GC) is the third most common lethal cancer in the world, and there are differences in the site of cancer occurrence depending on race, gender, and region, but recently, molecular genetic technology has made it possible to classify gastric cancer into different subtypes according to molecular characteristics.

Among biologically relevant subtypes of gastric cancer, especially those with stem-like characteristics have malignant biological characteristics that are difficult to treat and show the worst prognosis due to unresponsiveness to standard treatment (chemotherapy). In addition, as immune checkpoint blockade therapy has also been found to be ineffective against stem-like/EMT cancer subtypes, there is a problem in that targeted therapy cannot be applied to these cancer subtypes.

Accordingly, the present inventors have studied the molecular and metabolic characteristics of stem-like subtype GC, thereby developing a cancer therapeutic agent capable of effectively treating malignant gastric cancer.

DISCLOSURE

Technical Problem

An object of the present invention is to provide a pharmaceutical composition for preventing or treating cancer.

Another object of the present invention is to provide a pharmaceutical composition for inhibiting growth of cancer stem cells.

Still another object of the present invention is to provide a pharmaceutical composition for inhibiting cancer metastasis.

However, objects to be achieved by the present invention are not limited to the above-mentioned objects, and other objects not mentioned herein will be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the art to which the present invention pertains.

One embodiment of the present invention is directed to a composition for preventing, ameliorating or treating cancer comprising a myocardin-related transcription factor A (MRTF-A) inhibitor or a pharmaceutically acceptable salt thereof as an active ingredient.

The MRTF-A inhibitor of the present invention performs the function of inhibiting Rho/MRTF/SRF signaling, and may be at least one selected from the group consisting of CCG-232601, CCG-203971 and CCG-222740, but is not limited thereto and may be any type of inhibitor that performs this function.

In one embodiment of the present invention, CCG-232601 may be a compound represented by Formula 1 below, which is N-(4-chlorophenyl)-5,5-difluoro-1-(3-(pyridin-4-yl)benzoyl)piperidine-3-carboxamide. The compound CCG-232601 of the present invention is an inhibitor of the Rho/MRTF/SRF signaling pathway, is known as a potential anti-fibrotic therapeutic agent for systemic scleroderma, and is also known to suppress the development of bleomycin-induced dermal fibrosis when administered orally to mice.

[Formula 1]

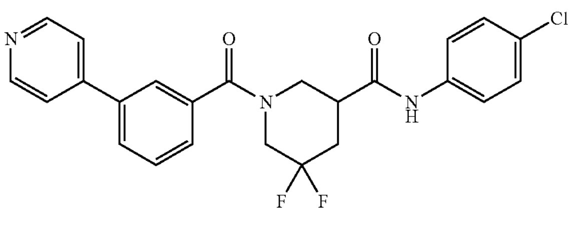

In another embodiment of the present invention, CCG-203971 may be a compound represented by Formula 2 below, which is N-(4-chlorophenyl)-1-(3-(furan-2-yl)benzoyl)piperidine-3-carboxamide. The compound CCG-203971 of the present invention is an inhibitor of the Rho/MKL1/SRF transcriptional pathway, and is known to play a role in the metastasis of melanoma and breast cancer and to be clinically related to prostate cancer, and the Rho/MRTF/SRF pathway is also known to be involved in several types of fibrosis. This compound inhibits both matrix stiffness and TGF-β-mediated fibrogenesis in human colonic myofibroblasts and exhibits anti-fibrotic activity in a murine model of skin injury and in lung fibrosis lung fibroblasts.

[Formula 2]

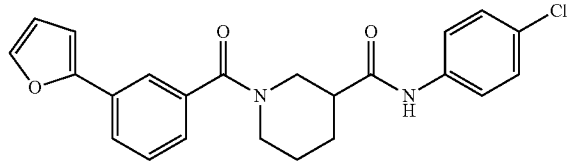

In another embodiment of the present invention, CCG-222740 may be a compound represented by Formula 3 below, which is N-(4-Chlorophenyl)-5,5-difluoro-1-(3-(furan-2-yl)benzoyl)piperidine-3-carboxamide. The compound CCG-222740 of the present invention is an MRTF/SRF inhibitor, and is known to prevent the expression of alpha smooth muscle actin protein, have low cytotoxicity, and effectively prevent scar tissue formation in a preclinical model of fibrosis.

[Formula 3]

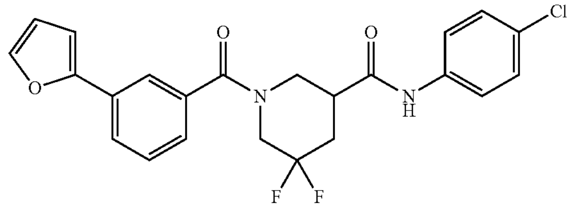

The compounds represented by Formulas 1 to 3 according to the present invention are capable of very effectively inhibiting growth of cancer cells and cancer stem cells. The composition of the present invention is capable of inhibiting the growth of cancer by inducing apoptosis of uncontrolled cells and inhibiting cell growth, and thus may be used very effectively for the prevention, amelioration or treatment of cancer.

Examples of the pharmaceutically acceptable salt of the present invention include acid or base addition salts, and stereochemically isomeric forms thereof. For example, the compounds may be in the form of organic or inorganic acid addition salts. The salts include any salts that have a desired effect on a patient when administered to the patient and retain the activities of their parent compounds, without being particularly limited thereto. Such salts include inorganic salts and organic salts, for example, salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, lactic acid, bicarbonic acid, bisulfuric acid, bitartaric acid, oxalic acid, butyric acid, calcium edetic acid, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic acid, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. Base addition salts include salts of alkali metals or alkaline earth metals, for example, salts of ammonium, lithium, sodium, potassium, magnesium, calcium, and the like; salts with organic bases, for example, salts of benzathine, N-methyl-D-glucamine, hydrabamine, and the like; and salts with amino acids such as arginine, lysine, and the like. In addition, these salts may be converted to free forms by treating the same with a proper base or acid.

A disease to be prevented, ameliorated or treated by the composition of the present invention may be cancer that has developed or is likely to develop in a subject of interest.

In the present invention, the "subject of interest" refers to mammals including humans, and may be selected from the group consisting of, for example, humans, rats, mice, guinea pigs, hamsters, rabbits, monkeys, dogs, cats, cows, horses, pigs, sheep, and goats, and preferably may be a human, without being limited thereto.

In the present invention, the "human" may refer to a person who has or is suspected of having cancer, and may mean a patient for whom appropriate cancer treatment is needed or expected, without being limited thereto.

In the present invention, the "cancer" as a disease to be prevented or treated refers to or describes the physiological condition in mammals that is typically characterized by unregulated cell growth. The cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvis carcinoma, central nervous system (CNS) tumor, primary CNS lymphoma, spinal cord tumor, brainstem glioma, or pituitary adenoma, but is not limited thereto and may be any type of tumor or cancer whose progression such as differentiation and/or proliferation is dependent on the cancer cells or cancer stem cells described in the present invention.

The cancer in the present invention may be at least one selected from the group consisting of gastric cancer, breast cancer, colorectal cancer, lung cancer, liver cancer, esophageal cancer, pancreatic cancer, gallbladder cancer, kidney cancer, bladder cancer, prostate cancer, testicular cancer, colon cancer, cervical cancer, endometrial cancer, chorionic cancer, skin cancer, ovarian cancer, thyroid cancer, brain cancer, blood cancer, head and neck cancer, malignant melanoma, and lymphoma, and preferably may be gastric cancer, without being limited thereto.

The term "prevention" in the present invention may include, without limitation, any action that blocks, suppresses or delays symptoms, caused by uncontrolled growth of cancer cells, by using the composition of the present invention.

The term "amelioration" in the present invention may include, without limitation, any action that alleviates or beneficially changes symptoms, caused by uncontrolled growth of cancer cells, by using the composition of the present invention.

The term "treatment" in the present invention may include, without limitation, any action that alleviates or beneficially changes symptoms, caused by uncontrolled growth of cancer cells, by using the composition of the present invention.

The composition for preventing, ameliorating or treating cancer according to the present invention may be used as a pharmaceutical composition or a food composition, without being limited thereto.

In the present invention, the pharmaceutical composition may be in the form of capsule, tablet, granule, injection, ointment, powder or beverage, and the pharmaceutical composition may be for administration to humans.

For use, the pharmaceutical composition of the present disclosure may be formulated in the form of, but not limited to, oral preparations, such as powders, granules, capsules, tablets, and aqueous suspensions, as well as external preparations, suppositories, and sterile injectable solutions, according to the respective conventional methods. The pharmaceutical composition of the present invention may comprise pharmaceutically acceptable carriers. As the pharmaceutically acceptable carriers, a binder, a lubricant, a disintegrant, an excipient, a solubilizer, a dispersant, a stabilizer, a suspending agent, a colorant, a flavoring agent, and the like may be used for oral administration; a buffer, a preservative, a pain-relieving agent, a solubilizer, an isotonic agent, a stabilizer, and the like may be used for injection; and a base, an excipient, a lubricant, a preservative, and the like may be used for topical administration. In addition, the pharmaceutical composition of the present invention may be prepared in various dosage forms by being mixed with the pharmaceutically acceptable carriers as described above. For example, for oral administration, the pharmaceutical composition may be formulated in the form of tablets, troches, capsules, elixirs, suspensions, syrups, wafers, or the like. For injection, the pharmaceutical composition may be formulated in the form of unit dosage ampoules or in multiple-dosage forms. In addition, the pharmaceutical composition may be formulated into solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present invention may further comprise a filler, an anticoagulant, a lubricant, a wetting agent, a fragrance, an emulsifier, a preservative, or the like.

The routes of administration of the pharmaceutical composition according to the present invention include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

In the present invention, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present invention may also be formulated as suppositories for intrarectal administration.

The administration dose of the pharmaceutical composition of the present invention may vary depending on various factors, including the activity of a specific compound used, the patient's age, body weight, general health, sex, diet, the time of administration, the route of administration, excretion rate, the drug content, and the severity of a specific disease to be prevented or treated. Although the dose of the pharmaceutical composition varies depending on the patient's condition, body weight, the severity of the disease, the form of drug, and the route and duration of administration, it may be suitably selected by a person skilled in the art and may be 0.0001 to 50 mg/kg/day or 0.001 to 50 mg/kg/day. The pharmaceutical composition may be administered once or several times a day. The dose is not intended to limit the scope of the present invention in any way. The pharmaceutical composition according to the present invention may be formulated as pills, sugar-coated tablets, capsules, liquids, gels, syrups, slurries, or suspensions.

In the present invention, the food composition is used in various ways for the prevention or amelioration of the target disease of the present invention, and may be prepared in the form of various foods, such as beverages, gums, teas, vitamin complexes, powders, granules, tablets, capsules, confectionery, rice cakes, bread, etc. The food composition of the present invention is an improved food composition based on existing food components having little or no toxicity and side effects, and thus may be used with confidence even when it is taken for a long period of time for preventive purposes. When the composition of the present invention is comprised in the food composition, it may be added in an amount of 0.1 to 100 wt % based on the total weight. When the food composition is prepared in the form of a beverage, there is no particular limitation, except that the beverage contains the food composition at the indicated percentage. The beverage may additionally contain various flavorings or natural carbohydrates, like conventional beverages. Examples of the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, and stevia extracts, such as rebaudioside A, glycyrrhizin, etc.) and synthetic flavorings (saccharin, aspartame, etc.). In addition, the food composition of the present invention may contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents that are used in carbonated beverages, etc. Such components may be used individually or in combination. The content of such additives is generally selected in a range of 0.1 to about 100 parts by weight based on 100 parts by weight of the composition of the present invention, without being limited thereto.

In addition, the composition for preventing, ameliorating or treating cancer according to the present invention may be administered in combination with other additional anticancer agent. Co-administration with other anticancer agent as described above can exert a remarkable effect on the prevention or treatment of cancer by more effectively inhibiting cancer growth or metastasis.

The anticancer agent in the present invention may be at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracin, oteracil, azacitidine, methotrexate, uracil, cytarabine, fluorouracil, fludagabine, enocitabine, flutamide, capecitabine, decitabine, mercaptopurine, thioguanine, cladribine, carmofur, raltitrexed, docetaxel, paclitaxel, irinotecan, belotecan, topotecan, vinorelbine, etoposide, vinblastine, idarubicin, mitomycin, bleromycin, dactinomycin, pyrarubicin, aclarubicin, pepromycin, temsirolimus, temozolomide, busulfan, ifosfamide, cyclophosphamide, melparan, altretmine, dacarbazine, thiotepa, nimustine, chlorambucil, mitolactol, leucovorin, tretonin, exmestane, aminoglutethimide, anagrelide, olaparib, navelbine, fadrozole, tamoxifen, toremifene, testolactone, anastrozole, letrozole, vorozole, bicalutamide, lomustine, 5FU, vorinostat, entinostat, and carmustine, without being limited thereto.

The anticancer agent in the present invention may be at least one selected from the group consisting of cisplatin, carboplatin, and oxaliplatin, and more preferably may be cisplatin.

Another embodiment of the present invention is directed to a method for preventing or treating cancer comprising administering to a subject in need thereof a pharmaceutically effective amount of a composition comprising a myocardin-related transcription factor A (MRTF-A) inhibitor or a pharmaceutically acceptable salt thereof as an active ingredient.

The MRTF-A inhibitor of the present invention performs the function of inhibiting Rho/MRTF/SRF signaling, and may be at least one selected from the group consisting of CCG-232601, CCG-203971 and CCG-222740, but is not limited thereto and may be any type of inhibitor that performs this function.

In the present invention, the term "administering" means providing the compound of the present invention to the subject by any suitable method.

In the present invention, the term "subject" in need thereof may include both mammals and non-mammals. Here, examples of the mammals include, but are not limited to, humans, non-human primates such as chimpanzees, other ape or monkey species; livestock animals such as cattle, horses, sheep, goats, and pigs; domesticated animals such as rabbits, dogs or cats; laboratory animals, for example, rodents such as rats, mice, or guinea pigs. In addition, examples of the non-mammals in the present invention include, but are not limited to, birds or fish.

In the present invention, the formulation of the compound that is administered as described above is not particularly limited, and may be administered as a solid formulation, a liquid formulation, or an aerosol formulation for inhalation. Specifically, the compound may be administered as solid form preparations which are intended to be converted, shortly before use, to liquid form preparations for oral or parenteral administration. For example, the compound may be formulated and administered as oral dosage forms, including powders, granules, capsules, tablets, and aqueous suspensions, preparations for external use, suppositories, and sterile injectable solutions, without being limited thereto.

In addition, in the present invention, pharmaceutically acceptable carriers may be additionally administered together with the compound of the present invention. Here, as the pharmaceutically acceptable carriers, a binder, a lubricant, a disintegrant, an excipient, a solubilizer, a dispersant, a stabilizer, a suspending agent, a colorant, a flavoring agent, and the like may be used for oral administration; a buffer, a preservative, a pain-relieving agent, a solubilizer, an isotonic agent, a stabilizer, and the like may be used for injection; and a base, an excipient, a lubricant, a preservative, and the like may be used for topical administration. In addition, the compound of the present invention may be prepared in various dosage forms by being mixed with the pharmaceutically acceptable carriers as described above. For example, for oral administration, the compound may be formulated in the form of tablets, troches, capsules, elixirs, suspensions, syrups, wafers, or the like. For injection, the compound may be formulated in the form of unit dosage ampoules or in multiple-dosage forms. In addition, the compound may be formulated into solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present invention may further contain a filler, an anticoagulant, a lubricant, a wetting agent, a flavoring agent, an emulsifier, a preservative, or the like.

The routes of administration of the compound according to the present invention include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

In the present invention, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present invention may also be formulated as suppositories for intrarectal administration.

In the present invention, the term "pharmaceutically effective amount" refers to a sufficient amount of an agent to provide a desired biological result. Said result may be reduction and/or alleviation of a sign, symptom, or cause of a disease, or any other desired alteration of a biological system. For example, an "effective amount" for therapeutic uses is the amount of the compound disclosed in the present invention, which is required to provide a clinically significant reduction in the disease. An appropriate "effective amount" in any individual case may be determined by one of ordinary skill in the art using routine experimentation. Thus, the expression "effective amount" generally refers to an amount in which an active substance has a therapeutic effect. In the case of the present invention, the active substance serves as both an inhibitor of growth of cancer cells or cancer tumor cells and an agent for preventing, ameliorating or treating cancer.

The administration dose of the compound of the present invention may vary depending on various factors, including the activity of a specific compound used, the patient's age, body weight, general health, sex, diet, the time of administration, the route of administration, excretion rate, drug combination, and the severity of a particular disease to be prevented or treated. Although the dose of the compound varies depending on the patient's condition and body weight, the severity of the disease, the form of drug, the route of administration, and the duration of administration, it may be appropriately selected by a person skilled in the art. The compound may be administered at a dose of 0.0001 to 100 mg/kg/day or 0.001 to 100 mg/kg/day. The compound may be administered once or several times a day. The dose does not limit the scope of the present invention in any way. The compound according to the present invention may be formulated as pills, sugar-coated tablets, capsules, liquids, gels, syrups, slurries, or suspensions.

The compound of the present invention may be used alone or in combination with surgery, radiotherapy, hormone therapy, chemotherapy, and methods that use biological response modifiers.

In addition, the compound of the present invention may be used in combination with other additional anticancer agent. Here, the anticancer agent may be at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracin, oteracil, azacitidine, methotrexate, uracil, cytarabine, fluorouracil, fludagabine, enocitabine, flutamide, capecitabine, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleromycin, daunorubicin, dactinomycin, pyrarubicin, aclarubicin, pepromycin, temsirolimus, temozolomide, busulfan, ifosfamide, cyclophosphamide, melparan, altretmine, dacarbazine, thiotepa, nimustine, chlorambucil, mitolactol, leucovorin, tretonin, exmestane, aminoglutethimide, anagrelide, olaparib, navelbine, fadrozole, tamoxifen, toremifene, testolactone, anastrozole, letrozole, vorozole, bicalutamide, lomustine, vorinostat, entinostat, phenformin, metformin, talazoparib, and carmustine, without being limited thereto.

In the present invention, details regarding the MRTF-A inhibitors CCG-232601, CCG-203971 and CCG-222740, the pharmaceutically acceptable salt, cancer, etc. are the same as those described above with respect to the composition for preventing, ameliorating or treating cancer, and thus will be omitted to avoid excessive complexity of the specification.

Still another embodiment of the present invention is directed to a composition for inhibiting growth of cancer stem cells comprising a myocardin-related transcription factor A (MRTF-A) inhibitor or a pharmaceutically acceptable salt thereof as an active ingredient.

The MRTF-A inhibitor of the present invention performs the function of inhibiting Rho/MRTF/SRF signaling, and may be at least one selected from the group consisting of CCG-232601, CCG-203971 and CCG-222740, but is not limited thereto and may be any type of inhibitor that performs this function.

In the present invention, the MRTF-A inhibitor is preferably at least one selected from the group consisting of CCG-232601, CCG-203971 and CCG-222740. In the present invention, details regarding the MRTF-A inhibitors CCG-232601, CCG-203971 and CCG-222740, the pharmaceutically acceptable salt, cancer, etc. are the same as those described above with respect to the composition for preventing, ameliorating or treating cancer, and thus will be omitted to avoid excessive complexity of the specification.

The compounds represented by Formulas 1 to 3 according to the present invention are capable of treating cancer, and more specifically, inhibiting the growth of cancer stem cells very effectively. The composition of the present invention is capable of inducing the death of tumors having stem-like characteristics and effectively inhibiting the growth of cancer stem cells, and thus it may be used very effectively for preventing, improving or treating cancer.

In the present invention, the term "cancer stem cells" refers to cancer cells having the ability to generate a tumor. Cancer stem cells have the same characteristics as normal stem cells, and more specifically, have the ability to create all cell types found in various types of cancer. That is, cancer stem cells are distinguished from cancer cells that do not form tumors in that they are tumorigenic. Cancer stem cells generate tumors through self-renewal and differentiation capabilities, which are characteristics of stem cells in various cell types. In addition, cancer stem cells are differentiated from other populations in a tumor and cause recurrence and metastasis by generating new tumors. Unlike cancer cells, cancer stem cells have a problem in that the therapeutic effect is poor when general anticancer drugs are used. Therefore, through the development of a specific treatment method targeting cancer stem cells, it is possible to increase the survival rate and improve the quality of life of cancer patients, in particular, to prevent metastatic cancer.

In addition, the composition for inhibiting growth of cancer stem cells according to the present invention may be administered in combination with other additional anticancer agent. Co-administration with other anticancer agent as described above can exert a remarkable effect on the prevention or treatment of cancer by more effectively inhibiting growth of cancer stem cells.

The composition for inhibiting growth of cancer stem cells according to the present invention may be used as a pharmaceutical composition or a food composition, without being limited thereto.

In the composition for inhibiting growth of cancer stem cells according to the present invention, details regarding the type of MRTF-A inhibitor, the type of pharmaceutically acceptable salt, the type of cancer, the anticancer agent that may be administered in combination, the definition of the pharmaceutical composition or the food composition, etc. are the same as described above, and thus will be omitted to avoid excessive complexity of the specification.

Yet another embodiment of the present invention is directed to a method for inhibiting growth of cancer stem cells comprising administering to a subject in need thereof a pharmaceutically effective amount of a composition comprising a myocardin-related transcription factor A (MRTF-A) inhibitor or a pharmaceutically acceptable salt thereof as an active ingredient.

In the present invention, details regarding the MRTF-A inhibitor, the pharmaceutically acceptable salt, the pharmaceutically effective amount, administration, the cancer stem cells, etc. are the same as described above, and thus will be omitted to avoid excessive complexity of the specification.

Still yet another embodiment of the present invention is directed to a composition for inhibiting cancer metastasis comprising a myocardin-related transcription factor A (MRTF-A) inhibitor or a pharmaceutically acceptable salt thereof as an active ingredient.

The MRTF-A inhibitor of the present invention performs the function of inhibiting Rho/MRTF/SRF signaling, and may be at least one selected from the group consisting of CCG-232601, CCG-203971 and CCG-222740, but is not limited thereto and may be any type of inhibitor that performs this function.

In the present invention, the MRTF-A inhibitor is preferably at least one selected from the group consisting of CCG-232601, CCG-203971 and CCG-222740. In the present invention, details regarding the MRTF-A inhibitors CCG-232601, CCG-203971 and CCG-222740, the pharmaceutically acceptable salt, cancer, etc. are the same as those described above with respect to the composition for preventing, ameliorating or treating cancer, and thus will be omitted to avoid excessive complexity of the specification.

The compounds represented by Formulas 1 to 3 according to the present invention are capable of very effectively inhibiting metastasis of cancer, more specifically, metastasis of cancer cells and cancer stem cells.

The "cancer metastasis" in the present invention refers to a phenomenon in which tumor cells generated in a primary organ acquire new genetic traits necessary for metastasis as cancer progresses, and then invade blood vessels and lymph glands, circulate along the lymph, settle in tissues present in organs different from the primary organ, and then proliferate. For the purpose of the present invention, the composition according to the present invention is capable of inhibiting cancer metastasis by suppressing some or all of the stages in which cancer cells depart from the primary organ, invade blood vessels and lymph glands, and settle in other organs, and thus it may be used very effectively for the purpose of inhibiting cancer metastasis.

In addition, the composition for inhibiting cancer metastasis according to the present invention may be co-administered with other additional anticancer agent. Co-administration with other anticancer agent as described above can exert a remarkable effect on the prevention or treatment of cancer by more effectively inhibiting cancer metastasis.

The composition for inhibiting cancer metastasis according to the present invention may be used as a pharmaceutical composition or a food composition, without being limited thereto.

In the composition for inhibiting cancer metastasis according to the present invention, details regarding the type of MRTF A inhibitor, the type of pharmaceutically acceptable salt, the type of cancer, the anticancer agent that may be administered in combination, the definition of the pharmaceutical composition or the food composition, etc. are the same as described above with respect to in the composition for preventing, ameliorating or treating cancer, and thus will be omitted to avoid excessive complexity of the specification.

A further embodiment of the present invention is directed to a method for inhibiting cancer metastasis comprising administering to a subject in need thereof a pharmaceutically effective amount of a composition comprising a myocardin-related transcription factor A (MRTF-A) inhibitor or a pharmaceutically acceptable salt thereof as an active ingredient.

In the present invention, details regarding the MRTF-A inhibitor, the pharmaceutically acceptable salt, the pharmaceutically effective amount, administration, the cancer stem cells, etc. are the same as described above, and thus will be omitted to avoid excessive complexity of the specification.

Another further embodiment of the present invention is directed to a method for screening a candidate substance for inhibiting growth of cancer stem cells.

The method of the present invention may comprise selecting a myocardin-related transcription factor A (MRTF-A) inhibitor.

In the present invention, the MRTF-A inhibitor may be any type of inhibitor that performs the function of suppressing Rho/MRTF/SRF signaling, without being limited thereto.

The method of the present invention may further comprise selecting a drug having an effect of inhibiting growth of cancer stem cells from among the selected inhibitors.

In the method for screening a candidate substance for treatment of cancer stem cells according to the present invention, details regarding the MRTF-A inhibitor, cancer, cancer stem cells, etc. are the same as those described above with respect to the composition for preventing, ameliorating or treating cancer, and thus will be omitted to avoid excessive complexity of the specification.

Advantageous Effects

When the composition according to the present invention is used, it is capable of effectively inhibiting the growth of not only cancer cells but also cancer stem cells, and is also capable of significantly inhibiting the metastasis of cancer cells to other tissues. Thus, the composition may be used not only for the prevention, amelioration or treatment of cancer, but also as an inhibitor of cancer metastasis.

BEST MODE

Figure 1:
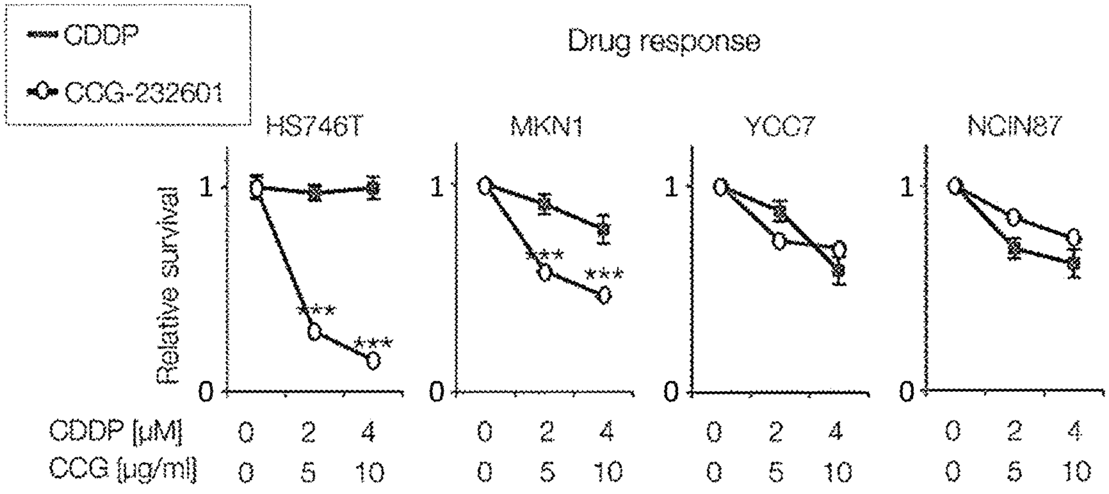
FIG. 1 shows the results of evaluating the inhibitory effects of cisplatin (CDDP) or CCG-232601 treatment against the survival and growth of cancer cell lines and cancer stem cell-like cell lines through a cell viability measurement method in one example of the present invention.

One embodiment of the present invention is directed to a composition for preventing or treating cancer comprising a myocardin-related transcription factor A (MRTF-A) inhibitor or a pharmaceutically acceptable salt thereof as an active ingredient.

Another embodiment of the present invention is directed to a method for preventing or treating cancer comprising administering to a subject in need thereof a pharmaceutically effective amount of a composition comprising a myocardin-related transcription factor A (MRTF-A) inhibitor or a pharmaceutically acceptable salt thereof as an active ingredient.

Still another embodiment of the present invention is directed to a pharmaceutical composition for inhibiting growth of cancer stem cells comprising a myocardin-related transcription factor A (MRTF-A) inhibitor or a pharmaceutically acceptable salt thereof as an active ingredient.

Yet another embodiment of the present invention is directed to a method for inhibiting growth of cancer stem cells comprising administering to a subject in need thereof a pharmaceutically effective amount of a composition comprising a myocardin-related transcription factor A (MRTF-A) inhibitor or a pharmaceutically acceptable salt thereof as an active ingredient.

Still yet another embodiment of the present invention is directed to a pharmaceutical composition for inhibiting cancer metastasis comprising a myocardin-related transcription factor A (MRTF-A) inhibitor or a pharmaceutically acceptable salt thereof as an active ingredient.

A further embodiment of the present invention is directed to a method for inhibiting cancer metastasis comprising administering to a subject in need thereof a pharmaceutically effective amount of a composition comprising a myocardin-related transcription factor A (MRTF-A) inhibitor or a pharmaceutically acceptable salt thereof as an active ingredient.

Another further embodiment of the present invention is directed to a method for screening a candidate substance for treatment of cancer stem cells, the method comprising steps of: selecting myocardin-related transcription factor A (MRTF-A) inhibitors; and selecting a drug having a therapeutic effect against cancer stem cells from among the selected inhibitors.

Mode for Invention

Hereinafter, the present invention will be described in more detail with reference to examples. It will be apparent to those of ordinary skill in the art that these examples serve merely to describe the present invention in more detail, and the scope of the present invention according to the subject matter of the present invention is not limited by these examples.

Preparation Example: Culture of Cell Lines

In order to evaluate the ability to inhibit the growth or metastasis of cancer cells or cancer stem cells in the examples according to the present invention, the present inventors obtained MKN1 and HS746T, which are cell lines having human gastric cancer stem cell characteristics, and SNU601, YCC7 and NCIN87 cells, which are human gastric cancer cell lines, from the American Type Culture Collection (ATCC) and the Korean Cell Line Bank (KCRB). The cell lines were cultured in different culture media and culture conditions according to ATCC's or KCRB's guidelines. The MKN1, SNU601, and NCIN87 cell lines were cultured in RPMI1640 medium containing 10% fetal bovine serum (FBS), 2 mM L-glutamine, 100 U/ml penicillin and 100 μg/ml streptomycin, and the HS746T and YCC7 Cell lines were cultured in DMEM containing 10% FBS, 2 mM L-glutamine, 100 U/ml penicillin and 100 μg/ml streptomycin. All the cell lines were cultured at 37° C. under 5% $CO_2$, and subjected to a *mycoplasma* contamination test.

Example 1: Evaluation of Therapeutic Effect of CCG-232601 Treatment Against Cancer Cells and Cancer Stem Cells Each of the cell lines cultured in the Preparation Example was dispensed into a well plate at a density of $1\times10^4$ cells per well, and cultured overnight at 37° C. under 5% $CO_2$. Then, the HS746T and MKN1 cell lines, which are gastric cancer stem-like cells, and the YCC7 and NCIN87 cell lines, which are gastric cancer cells, were treated with various concentrations of each of cisplatin (CDDP), which is an anticancer drug currently frequently used in the treatment of gastric cancer patients, and the compound CCG-232601 which is an MRTF-A inhibitor. After 48 hours, the cell numbers were measured and the results are shown in FIG. 1. 100 μL of each cell culture and 10 μL of reaction buffer (CCK) were mixed together, placed in a 96-well plate, and incubated for 1 hour at room temperature, and then the absorbance at a wavelength of 450 nm was measured using a spectrophotometer (Synergy HTX Multi-Reader, BioTek, Winooski, VT, USA). At the same time, the number of cells in each sample was measured with a cell viability assay kit (Cell Counting Kit-8), and the measured value was converted so that the measured value for the same number of cells in each sample could be compared with the number of cells in the negative control group. All experiments were repeated three times, and the results are shown in FIG. 1. The experimental results presented are the mean values of the repeated experiments.

As a result of the experiment, it was confirmed that treatment with the compound CCG-232601 alone exhibited antitumor effects against not only the cancer cells but also the cancer stem cells, and also exhibited significantly improved antitumor effects against the stem-like cell lines HS746T and MKN1 whose treatment with cisplatin alone did not exhibit antitumor effects due to the drug resistance of the cells (see FIG. 1). As such, it can be seen that the compound CCG-232601 according to the present invention can reduce the viability of cancer cells and cancer stem cells and inhibit the growth of the cells.

Figure 2:
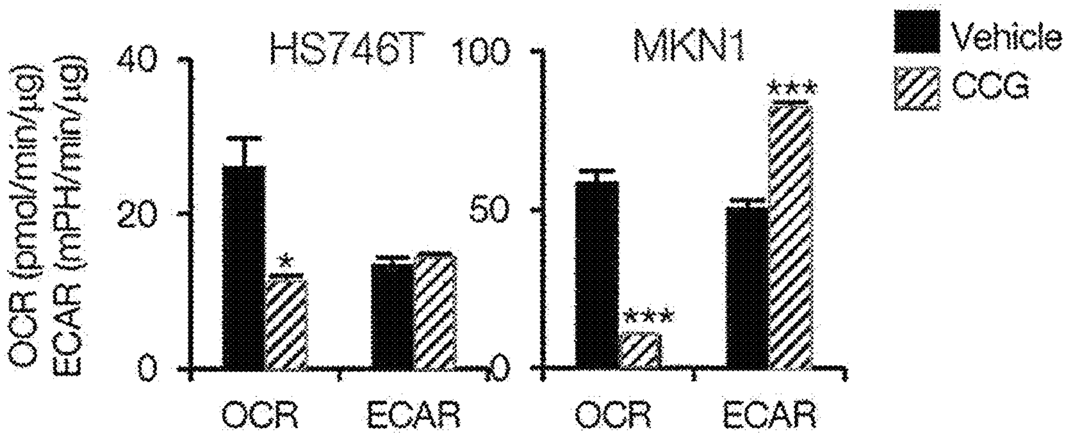
FIG. 2 shows the results of measuring the oxygen consumption rate (OCR) and extracellular acidification rate (ECAR) of cells after treatment of HS746T and MKN1 cell lines having cancer stem cell (s-cell) characteristics with CCG-232601 in one example of the present invention.

In particular, in order to confirm that the compound CCG-232601 has an excellent inhibitory effect on cancer stem cell growth, the oxygen consumption rates (OCRs) and extracellular acidification rates (ECARs) of the stem-like cell lines HS746T and MKN1 having high resistance to metabolic stress were measured and the results are shown in FIG. 2. More specifically, each of the cell lines was seeded in Seahorse normal culture medium at 70 to 80% confluency, and mitochondrial oxidation and glycolytic activity were measured by measuring oxygen consumption rate (OCR, pmol/min/μg protein) and extracellular acidification rate (ECAR, mpH/min/μg protein) using an XF96 or XFp extracellular flux analyzer (Agilent). Mitochondrial oxidation ability of cells pretreated for 1 hour with or without 10 mM β-HB (Sigma) was evaluated using the Seahorse XF mito stress kit (Agilent). To address changes in oxidation and glycolysis upon treatment with CCG-232601, cells were pretreated overnight with vehicle or the inhibitor, and finally 10 mM β-hydroxybutyrate was added during the first injection.

As a result of the experiment, it was confirmed that, when treated with CCG-232601, the glycolysis ECAR was higher than OCR, which is an indicator of mitochondrial respiration (see FIG. 2). Mitochondrial respiration is a metabolic feature of cancer stem cells, which is distinguished from glycolysis, a metabolic feature of rapidly dividing cancer cells. This result means that the dependence on glycolysis in the process of obtaining energy increased when treated with CCG-232601, suggesting that the representative metabolic feature of cancer stem cells changed when treated with CCG-232601.

Through the above results, it was confirmed that treatment with the compound CCG-232601 greatly increased the sensitivity to glucose deprivation in gastric cancer stem cells whose representative feature is resistance to metabolic stress.

Example 2: Evaluation of Cancer Metastasis Inhibitory Effect Upon Administration of CCG-232601

Figure 3:
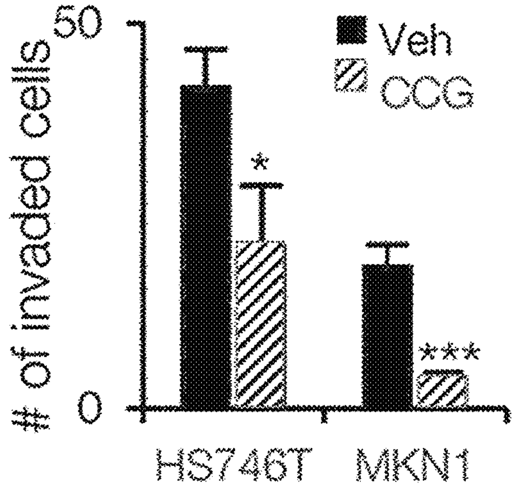
FIG. 3 shows the results of evaluating the cancer metastasis inhibitory effect of CCG-232601 treatment against HS746T and MKN1 cell lines having cancer stem cell (s-cell) characteristics in one example of the present invention.

Transwell invasion assay was performed with or without CCG-232601 treatment. The invasion ability was measured using a 6.5-mm transwell with an 8.0 μm-pore polycarbonate membrane insert (Corning) after coating with Matrigel (Corning) diluted to 0.67 μg/μl with serum-free medium. Then, cells ($2\times10^4$ cells/well) were suspended in 200 μL of a serum-free medium with vehicle or in 10 μg/ml of CCG-232601, and 1,000 μL of culture medium containing 10% FBS was added to the lower chamber. After 12 hours, the migrated cells were stained with 0.2% crystal violet and observed under an optical microscope. The average number of cells that penetrated the membrane was calculated with ImageJ (NIH) from three randomly selected high-power fields and from two independent experiments, and the results are shown in FIG. 3.

As a result of the experiment, it was confirmed that treatment with CCG-232601, an MRTFA/SRF inhibitor, reduced the invasion and metastasis of the HS746T and MKN1 cell lines.

From the above results, it can be seen that the compound according to the present invention can very effectively inhibit cancer cell invasion and cancer metastasis by inhibiting MRTFA/SRF of cancer cells.

Example 3: Evaluation of Drug Sensitivity Improvement Effect Upon Co-Administration of CCG-232601

Figure 4:
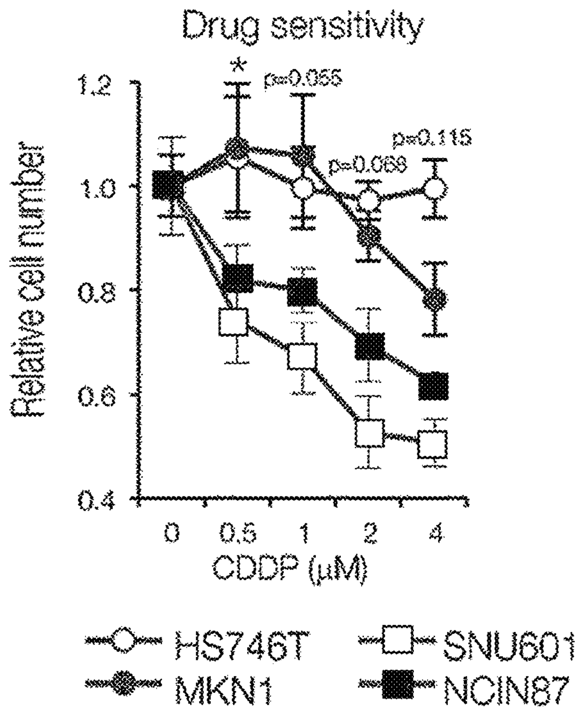
FIG. 4 shows the results of evaluating drug sensitivity after treatment of HS746T and MKN1 cell lines with cisplatin in one example of the present invention.

FIG. 3 shows the results of measuring drug sensitivity upon cisplatin (CDDP) treatment of SNU601 and NCIN87 cell lines, which are gastric cancer cell lines, and HS746T and MKN1 cell lines, which have characteristics similar to those of gastric cancer stem cells. As a result of the experiment, it could be confirmed that the HS746T and MKN1 cell lines, which are relatively cancer stem-like cell lines, exhibited resistance to cisplatin, and that the drug sensitivity of the cancer stem cell lines was about 20 to 40% lower than that of the cancer cell lines (see FIG. 4).

Figure 5:
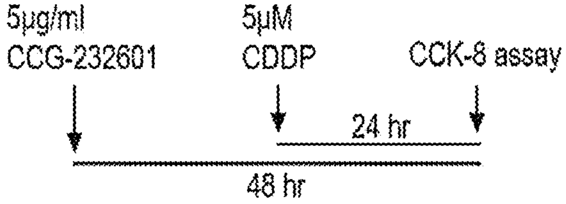
FIG. 5 is a schematic view showing treating the MKN1 cell line with a combination of CCG-232601 and cisplatin in one example of the present invention.

Accordingly, in order to evaluate the effect of co-administration of the compound CCG-232601, the survival and growth inhibitory effects of administration of CCG-232601 and cisplatin (CDDP) alone or in combination to the MKN1 cell line were evaluated using a cell viability assay kit (Cell Counting Kit-8; CCK-8). A schematic view of a specific experimental process for this evaluation is shown in FIG. 5. In order to evaluate the effect of administration in combination compared to that of administration alone, 5 μg/ml of CCG-232601 was firstly administered to the MKN1 cell line, and after 24 hours, 5 μM cisplatin (CDDP) was secondarily administered. After 24 hours therefrom, the results were checked with a cell viability analysis kit (CCK-8 assay).

Figure 6:
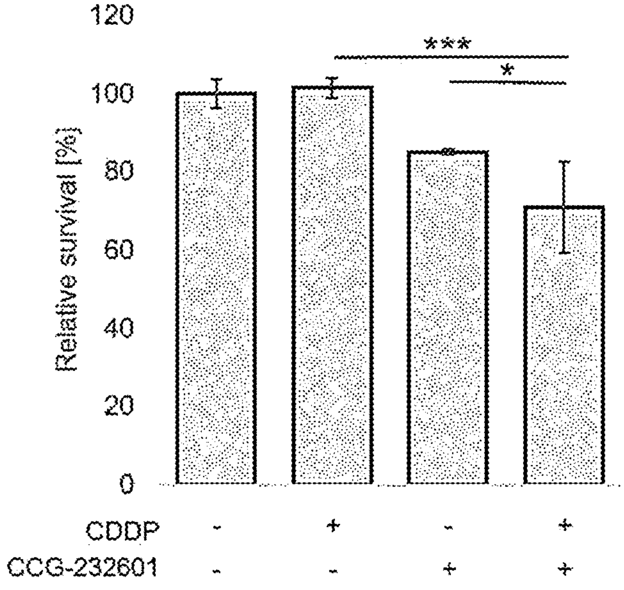
FIG. 6 shows the results of evaluating the inhibitory effects of treatment with CCG-232601 and cisplatin alone or in combination against the survival and growth of the MKN1 cell line by the use of a cell viability assay kit (Cell Counting Kit-8; CCK-8) in one example of the present invention.

As a result of the experiment, it was confirmed that the cell viability of the MKN1 cell line having cancer stem cell characteristics was 20% lower in the group to which only the compound CCG-232601 according to the present invention was administered alone than in the negative control group and the group to which only cisplatin was administered. In addition, it can be confirmed that the drug resistance that appeared when cisplatin was administered alone was overcome when co-treated with the compound CCG-232601 (see FIG. 6).

Taken together, the above results suggest that the compound CCG-232601 according to the present invention can exhibit a synergistic effect with an anticancer agent, particularly cisplatin, on the inhibition of cancer stem cell growth, and can also overcome resistance to cisplatin.

Example 4: Evaluation of Therapeutic Effects of Other MRTFA/SRF Inhibitors Against Cancer Stem Cells The present inventors attempted to further confirm the therapeutic effects of the compounds CCG-222740 and CCG-203971, which are compounds other than the compound CCG-232601 corresponding to the MRTFA/SRF inhibitors, against cancer stem cells. As reviewed in Example 1 above, it has been confirmed that the gastric cancer cell line HS746T is of a stem cell-like gastric cancer type, and thus is resistant to the anticancer drug cisplatin. The HS746T cell line was treated with cisplatin and the compounds CCG-222740 and CCG-203971 corresponding to MRTFA/SRF inhibitors. For cell treatment, cisplatin was used at concentrations of 0 μM, 5 μM and 10 μM, and the compound CCG-222740 or CCG-203971 was used at concentrations of 0 μg/ml, 5 μg/ml and 10 μg/ml. The control group was treated with the same amount of DMSO as the compound used for each experimental group. After 48 hours, the number of living cells was measured using a cell viability assay kit (Cell Counting Kit-8), and the results are shown in FIGS. 7A and 7B.

Figure 7A:
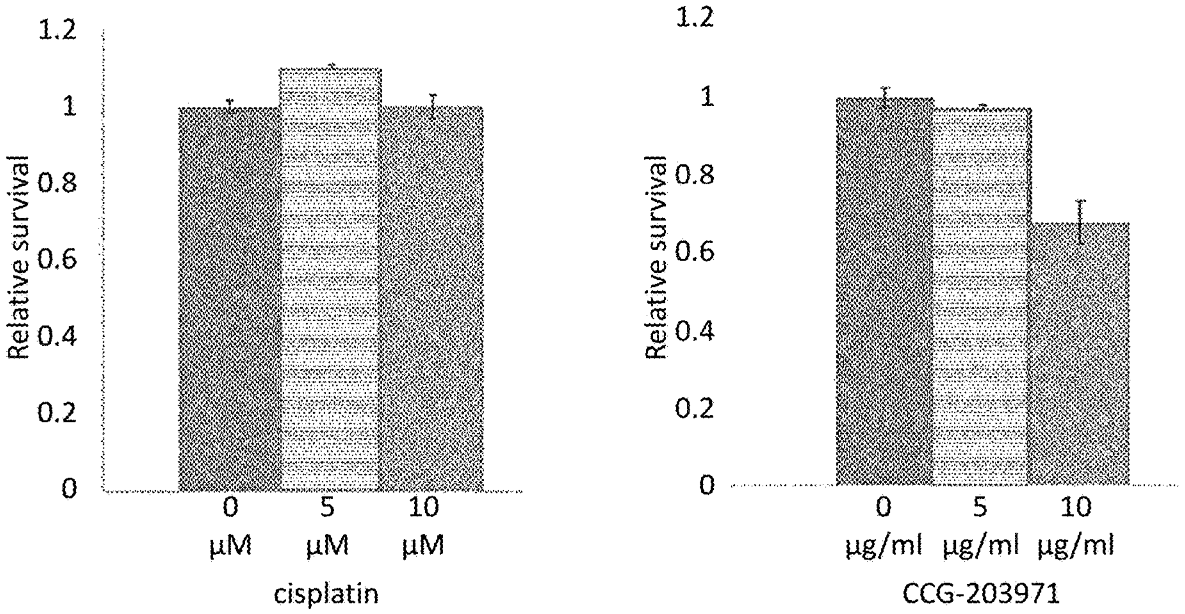
FIGS. 7A and 7B show the results of evaluating the inhibitory effects of treatment with cisplatin, CCG-203971 or CCG-222740 alone against the survival and growth of the HS746T cell line by the use of a cell viability assay kit in one example of the present invention.
Figure 7B:
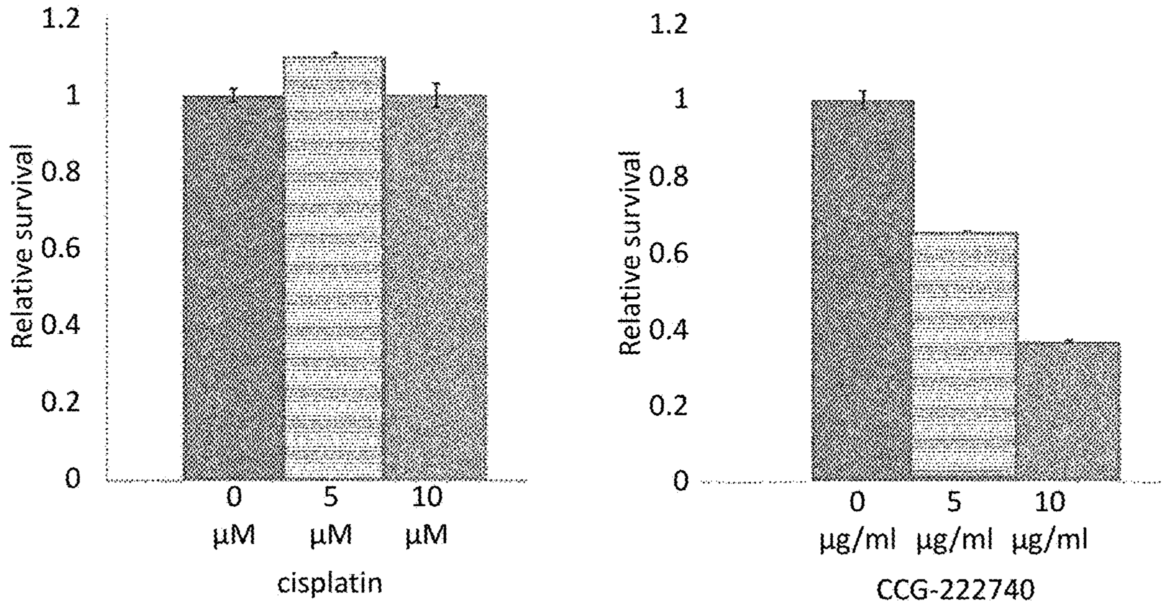

As a result of the experiment, it was confirmed that treatment with the compound CCG-222740 or CCG-203971 alone exhibited a significantly improved antitumor effect against the HS746T cell line, which is the stem-like cell line whose treatment with cisplatin alone did not exhibit an antitumor effect due to its drug resistance (see FIGS. 7A and 7B). As such, it can be seen that the compound CCG-222740 or CCG-203971 according to the present invention can reduce the viability of cancer stem cells and inhibit the growth thereof.

Taken together, it is expected that the use of the composition according to the present invention is able to effectively treat subtypes of gastric cancer, especially gastric cancer with stem-like characteristics, ultimately contributing to improvement in survival rate.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

When the composition according to the present invention is used, it is capable of inhibiting the growth of cancer stem cells and is also capable of very effectively inhibiting the metastasis of cancer cells to other tissues, thereby very effectively preventing, ameliorating or treating gastric cancer, particularly gastric cancer of the stem-like subtype.

The invention claimed is:

1. A method for treating stem-like subtype gastric cancer comprising administering to a subject in need thereof, as an active ingredient, a pharmaceutical composition comprising a myocardin-related transcription factor A (MRTF-A) inhibitor or a pharmaceutically acceptable salt thereof, wherein the inhibitor is at least one selected from the group consisting of compounds represented by Formulas 1 to 3 below:

[Formula 1]

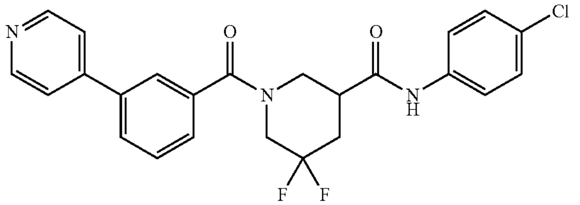

[Formula 2]

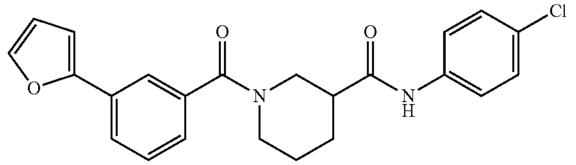

[Formula 3]

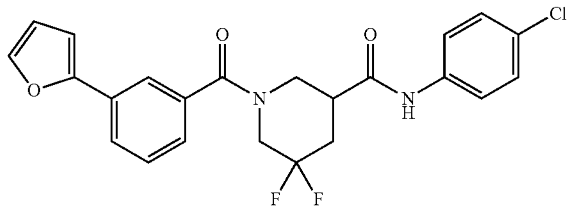

2. The method according to claim 1, wherein the pharmaceutical composition further comprises at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracin, oteracil, azacitidine, methotrexate, uracil, cytarabine, fluorouracil, fludagabine, enocitabine, flutamide, capecitabine, decitabine, mercaptopurine, thioguanine, cladribine, carmofur, raltitrexed, docetaxel, paclitaxel, irinotecan, belotecan, topotecan, vinorelbine, etoposide, vinblastine, idarubicin, mitomycin, bleromycin, dactinomycin, pyrarubicin, aclarubicin, pepromycin, temsirolimus, temozolomide, busulfan, ifosfamide, cyclophosphamide, melparan, altretmine, dacarbazine, thiotepa, nimustine, chlorambucil, mitolactol, leucovorin, tretonin, exmestane, aminoglutethimide, anagrelide, olaparib, navelbine, fadrozole, tamoxifen, toremifene, testolactone, anastrozole, letrozole, vorozole, bicalutamide, lomustine, 5FU, vorinostat, entinostat, and carmustine.

3. The method according to claim 1, wherein the inhibitor is a compound represented by Formula 1 below:

[Formula 1]

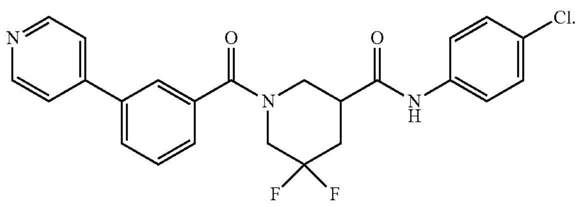

4. The method according to claim 1, wherein the inhibitor is a compound represented by Formula 2 below:

[Formula 2]

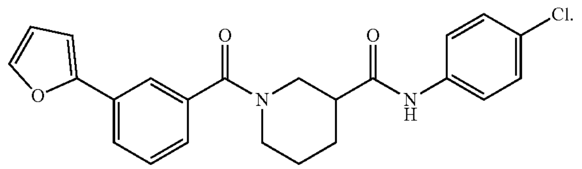

5. The method according to claim 1, wherein the inhibitor is a compound represented by Formula 3 below:

[Formula 3]

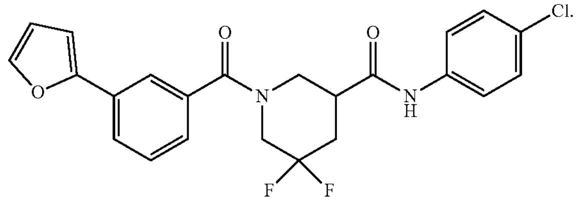

* * * * *